United States Patent [19]

Lotus et al.

[11] Patent Number: 4,939,250
[45] Date of Patent: Jul. 3, 1990

[54] PROCESS FOR PREPARATION OF β-LACTAM DERIVATIVES

[75] Inventors: Frank Loftus; Stephen J. Pegg, both of MacClesfield; Evan W. Snape, Congleton, all of United Kingdom

[73] Assignee: Imperial Chemical Industries Plc, London, England

[21] Appl. No.: 48,882

[22] Filed: May 12, 1987

[30] Foreign Application Priority Data

May 15, 1986 [GB] United Kingdom ............... 86 11823

[51] Int. Cl.$^5$ ........................................... C07D 501/04
[52] U.S. Cl. .................................... 540/222; 540/225; 540/226; 540/227; 540/300; 540/301; 540/350
[58] Field of Search ............... 540/222, 227, 226, 350, 540/300, 301

[56] References Cited

U.S. PATENT DOCUMENTS

| 4,464,368 | 8/1984 | O'Callaghan et al. | 540/222 |
|---|---|---|---|
| 4,678,781 | 7/1987 | Jung | 514/200 |
| 4,748,171 | 5/1988 | Yamauchi et al. | 540/222 |

OTHER PUBLICATIONS

J. Org. Chem. 1988, 53, 983–991.
Merck Index, p. 271.
Merck Index, p. 276.

Primary Examiner—Nicholas S. Rizzo
Attorney, Agent, or Firm—Cushman, Darby & Cushman

[57] ABSTRACT

A process for preparing compounds of the formula I:

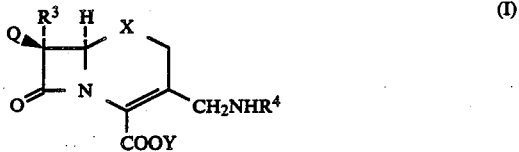

wherein X is sulphur, oxygen, methylene or sulphinyl (R or S configuration), $R^3$ is hydrogen or methoxy, $R^4$ is an optionally substituted (1-4C)alky group, Y is hydrogen or a carboxyl protecting group and Q is an optionally protected amino group or an acylamino group, which comprises reacting a compound of formula (II)

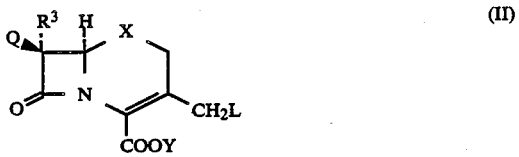

with a compound of formula (III)

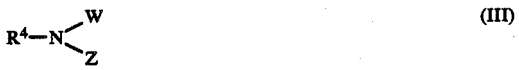

wherein $R^4$ is as defined above and W and Z represent hydrogen atoms or a group or groups removable to yield the compound of formula (I). The compounds of the formula I are useful intermediates in the preparation of cephalosporin antibiotics.

9 Claims, No Drawings

PROCESS FOR PREPARATION OF β-LACTAM DERIVATIVES

The invention relates to improvements in or relating to processes for the manufacture of cephalosporin derivatives which are intermediates for antibiotic compounds.

Our published European Patent Application No. 164944 describes certain cephalosporin derivatives having antibiotic activity. It is a feature of the said derivatives that they contain an aminomethyl group at the 3-position of the cephalosporin nucleus, the said aminomethyl group being substituted by one of a number of defined heterocyclic ring systems which are linked via carbon, and which contain a quaternised nitrogen atom. The aminomethyl group may further be substituted by an alkyl, substituted alkyl or allyl group. It is an object of this invention to provide a method whereby intermediates in the manufacture of such compounds may be prepared.

Accordingly the invention provides a process for the preparation of compounds of formula I:

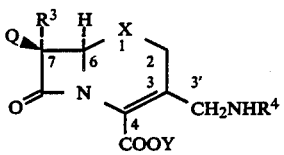

(I)

and salts thereof wherein
X is sulphur, oxygen, methylene or sulphinyl (R or S configuration);
$R^3$ is hydrogen or methoxy;
$R^4$ is (1–4C)alkyl, halo(1–4C)alkyl, hydroxy(1–4C)alkyl, (1–4C)alkoxy(1–4C)alkyl, carboxy(1–4C)alkyl, amino (1–4C)alkyl, cyano(1–4C)alkyl, (1–4C)alkanoyl-amino(1–4C)alkyl, allyl, furfuryl, benzyl or pyridyl(1–4C)alkyl;
Y is hydrogen or a carboxyl protecting group; and Q has one of the following meanings,
 (i) an amino group:
 (ii) a protected amino group,
 (iii) a group required at the equivalent position in the final cephalosporin antibiotic or a precursor of such a group;
 (iv) an acylamino group not falling within (iii) above but which can readily be converted to an amino group;
which process includes the step of reacting a compound of formula II:

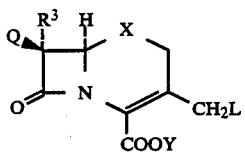

(II)

wherein Q, X, Y and $R^3$ are as hereinbefore defined and L is a leaving group, with a compound of formula III:

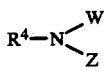

(III)

wherein $R^4$ is as hereinbefore defined and W and Z independently represent hydrogen atoms or groups removable in the initial or in a subsequent reaction step to yield the compound of the formula (I) or W and Z are joined together to form a group removable in the initial or in a subsequent reaction step to yield the compound of the formula (I).

In a preferred aspect of the invention W and Z (which may be the same or different) represent groups joined to the nitrogen atom of the compound of the formula (III) by a single bond, for example a group $ArCH_2$, $Ar_2CH$, ArS, a sulphonyloxy group such as $SO_3R^a$, a carboxy group such as $CO_2R^b$ or a silyl moiety such as $SiR^cR^dR^e$, wherein $R^a$, $R^b$, $R^c$, $R^d$ and $R^e$ independently represent $C_{1-4}$ alkyl groups and Ar represents an aryl group; or one of W and Z represents such a group and the other is hydrogen.

In another preferred aspect W and Z are each joined to the nitrogen atom by single bonds and are themselves joined so as to form a cyclic structure; for example a triazine of the formula IV:

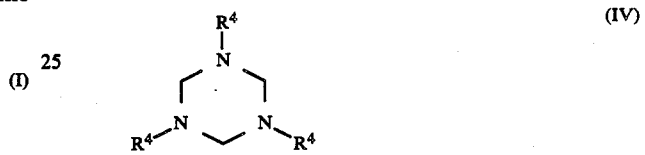

(IV)

wherein $R^4$ is as hereinbefore defined, or a compound of formula IVa:

(IVa)

wherein $R^4$ is as hereinbefore defined, or IVb:

(IVb)

wherein $R^4$, $R^a$ and $R^b$ are as hereinbefore defined.

In a further preferred aspect W and Z together represent a group joined to the nitrogen atom of the compound of formula III by a double bond, for example an alkylidene group or a group of the formula ArCH=, $ArC(R^a)=$ or $(Ar)_3P=$ wherein Ar and $R^a$ are as hereinbefore defined or a group of formula IVc:

(IVc)

wherein $R^f$ and $R^g$ represent (1–4C)alkyl groups. Where W and/or Z contains the group Ar, this may be a carbocyclic or heterocyclic aryl group for example a phenyl, thienyl or furyl group and may be substituted, e.g. by one or more groups selected from halogen, nitro, cyano, (1–6C)alkyl, hydroxy, amino, (1–4C)alkoxy, carboxy, (2–6C)alkoxycarbonyl, carbamoyl, mono-or di(1–4C)alkylcarbamoyl and aminomethyl groups.

Where W and Z both represent hydrogen, the process of the invention leads directly to the desired compound of formula I. Where either or both of W and Z are other than hydrogen, they must be removed in the initial or in a subsequent reaction step to yield the compound of formula I. W and Z are preferably such that their removal takes place under relatively mild conditions in a single step.

Removal of W and Z may thus occur, under appropriate conditions, as part of the initial step of reaction of the compounds of formulae II and III or the reaction may produce an intermediate of formula Ia:

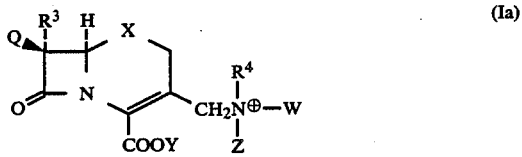

Wherein Q, $R^3$, H, $R^4$, W, Z and Y are as hereinbefore defined and wherein a counter-ion is present or the compound of formula (Ia) is in the form of a zwItterion. This is then subjected to a further reaction step (e.g. hydrolysis or hydrogenolysis) to yield the compound of formula I. It will generally be convenient to proceed without isolation of an intermediate of formula Ia which may, under certain conditions, be formed only as a transient species.

Removal of W and Z may take place by conventional methods e.g. by hydrolysis or hydrogenolysis for example aqueous, acid or weakly basic hydrolysis, or hydrogenolysis using a catalyst e.g. palladium/carbon or Raney nickel. For certain meanings of W and Z it may be sufficient simply to add water to the reaction mixture, and this is of course especially convenient.

Preferred meanings for W and Z are:
(i) W represents hydrogen and Z represents a group $ArCH_2$ in particular benzyl or substituted benzyl;
(ii) W and Z are joined to complete a triazine of formula IV;
(iii) W and Z together represent a group ArCH= where Ar represents phenyl or substituted phenyl.

The leaving group L in formula II may be any group which can be displaced by the compound of formula III under the conditions of the reaction, preferably in a single step under relatively mild conditions. Conveniently the reaction between the compounds of the formulae II and III takes place in a solvent such as a polar aprotic solvent for example dimethylformamide or acetonitrile, or in a chlorinated hydrocarbon for example dichloromethane, 1,2-dichloroethane or chloroform. Conveniently the reaction is carried out at a non-extreme temperature for example between −30° C. and +50° C. and typically in the range −10° C. to 25° C. Most conveniently the reaction is conducted at room temperature. Preferably the reaction is performed under substantially anhydrous conditions, particularly where W and/or Z are groups removable by hydrolysis as we have found it preferable to form the intermediate (Ia) prior to the removal of groups W and Z.

Examples of leaving groups L include acyloxy (e.g. acetoxy, propionyloxy, chloroacetoxy, dichloroacetoxy and acetoacetoxy) groups; halogen (e.g. chlorine, bromine and iodine) atoms; and carbamoyloxy, alkylthio (e.g. methylthio), cyanothio, dialkylsulphonio (e.g. di(-1–4C)alkylsulphonio particularly dimethylsulphonio), substituted-alkane sulphonyloxy (e.g. trifluoromethane or 1,1,2,2-tetrafluoroethane sulphonyloxy) and o-phenylenephosphonyloxy groups.

The process of the invention wherein the leaving group L is an acyloxy group, particularly an acetoxy group, may be facilitated if the reaction is carried out in the presence of iodide or thiocyanate ions, provided for example by the addition of an appropriate salt (e.g. sodium or potassium iodide or thiocyanate) to the reaction mixture, as described for example in British Patent Specifications Nos. 1132621 and 1171603.

The process of the invention may also be carried out by reacting a compound of formula II wherein L is acyloxy, particularly an acetoxy group, with the compound of formula III in the presence of a tri-alkylsilyl iodide, e.g. trimethylsilyl iodide or t-butyl-dimethylsilyl iodide. Such a reaction may proceed via the corresponding compound of formula II wherein L is iodine, and this compound may be isolated if desired, but it is generally convenient to proceed without isolation of the 3-iodomethyl compound, which is reacted with the compound of formula III in situ. The use of a trialkylsilyl iodide in this manner is described for example in U.S. Pat. No. 4,266,049.

The process of the invention may also be carried out by reacting a compound of formula II in which L is acyloxy, particularly an acetoxy group; with the compound of formula III in the presence of an alkane sulphonate derivative for example a trialkylsilyl substituted methane or ethanesulphonate such as trimethylsilyl trifluoromethanesulphonate, triisopropylsilyl trifluoromethanesulphonate or tri-methylsilyl 1,1,2,2-tetrafluoroethanesulphonate.

It will be appreciated that the identity of the leaving group L, provided that it is readily displaceable under the conditions of the reaction, is not critical, as it forms no part of the reaction product. Any displaceable group may be employed whether or not it is a group normally employed as a leaving group in cephalosporin chemistry. For example, the 3-pyridinium group found in cephalosporin antibiotics such as cephaloridine and ceftazidime and heterocyclicthio groups found in certain other known cephalosporin antibiotics may function as leaving groups in the process of the invention and the use therein of compounds of this type is within the scope of the invention.

As stated hereinbefore the reaction of the compounds of the formulae (II) wherein L is acyloxy with the compounds of the formula (III) may be performed in the presence of a trialkylsilyl halide and this can form in situ an acid, for example hydrogen iodide. Such acids may have an undesirable effect on the starting materials and product of the reaction, so we have found it useful to include an acid scavenger in the reaction mixture. Epichlorohydrin is a particularly useful acid scavenger. Acid scavengers such as epichlorohydrin may also serve to desilylate any silyl esters present and advantageously will scavenge any excess of species such as trialkylsilyl halides.

Preferred meanings for the leaving group L are an iodine atom or an acetoxy, thiocyanate (cyanothio) or dimethylsulphonio group.

It is to be understood that in the above formula I and throughout this specification the illustrated stereochemistry of the ceph-3-em nucleus, and its optional modifications at the 1-position, is the absolute configuration.

It will also be understood that the compounds of formula (I) wherein Y represents H may exist in equilibrium with the zwitterionic form in which the 4 carboxylic acid function is deprotonated to form a carboxylate anion and the 3'-substituted amino group is protonated. Such zwitterionic forms are within the scope of formula (I).

When a salt of the compound of formula I is required, the compound of formula I may be reacted with an appropriate acid or base.

Salts of the compounds of formula (I) which may be prepared include acid- and base- addition salts e.g. alkali metal (e.g. sodium and potassium) salts and salts with organic acids e.g. p-toluenesulphonic acid.

Preferably the group X is sulphur: $R^3$ is preferably hydrogen.

Particular meanings for the group $R^4$ are methyl, ethyl, n-propyl, isopropyl, 2-fluoroethyl, 2-chloroethyl, 2-hydroxyethyl, 2-methoxyethyl, carboxymethyl, (R) and (S)-1-carboxyethyl, 2-aminoethyl, 2-cyanoethyl, 2-formamidoethyl, allyl, furfuryl, benzyl and 4-pyridylmethyl. Compounds wherein $R^4$ is methyl or ethyl, especially ethyl, are particularly advantageous.

When reference is made to protecting groups being present at any position in the compounds described herein such protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course wIthIn the scope of the invention.

Examples of carboxyl protecting groups include straight or branched chain (1–12C)alkyl groups (e.g. isopropyl, t-butyl); halo lower alkyl groups (e.g. 2-iodoethyl, 2,2,2-trichloroethyl); lower alkoxy lower alkyl groups (e.g. methoxymethyl, ethoxymethyl, isobutoxymethyl); lower aliphatic acyloxy lower alkyl groups, (e.g. acetoxymethyl, propionyloxymethyl, butyryloxymethyl, pivaloyloxymethyl); lower alkoxycarbonyloxy lower alkyl groups (e.g. 1-methoxycarbonyloxyethyl, 1-ethoxycarbonyloxyethyl); aryl lower alkyl groups (e.g. p-methoxybenzyl, o-nitrobenzyl, p-nitrobenzyl, benzhydryl and phthalidyl); tri(lower alkyl)silyl groups (e.g. trimethylsilyl and t-butyldimethylsilyl); tri(lower alkyl)silyl lower alkyl groups (e.g. trimethylsilylethyl); and (2–6C)alkenyl groups (e.g. vinylethyl).

Methods particularly appropriate for the removal of carboxyl protecting groups include for example acid-, base- or enzymically-catalysed hydrolysis.

Examples of amino protecting groups include aryl lower alkyl groups (e.g. benzyl and substituted benzyl, e.g. p-methoxybenzyl and 2,4-dimethoxybenzyl, and triphenylmethyl); di-p-anisylmethyl and furylmethyl groups; acyl (e.g. formyl, lower alkoxycarbonyl and aryl lower alkoxycarbonyl e.g. t-butoxycarbonyl and benzyloxycarbonyl); tri lower alkylsilyl (e.g. trimethylsilyl and t-butyldimethylsilyl); lower alkylidene (e.g. methylidene); benzylidene and substituted benzylidene groups; and the phthalimido group.

Carboxyl and amino protecting groups may be removed at any convenient stage of the reaction by appropriate methods e.g. as described in the literature.

Where Q represents a group required at an equivalent position in the final cephalosporin antibiotic it may be for example a group of the formula V:

in which the $OR^2$ group has the syn configuration and wherein $R^1$ is 2-aminothiazol-4-yl or 2-aminooxazol-4-yl each optionally substituted in the 5-position by fluorine, chlorine or bromine, or $R^1$ is 5-aminoisothiazol-3-yl, 5-amino-1,2,4-thiadiazol-3-yl, 3-aminopyrazol-5-yl, 3-aminopyrazol-4-yl, 2-amino-pyrimidin-5-yl, 2-aminopyrid-6-yl, 4-aminopyrimidin-2-yl, 2-amino-1,3,4-thiadiazol-5-yl or 5-amino-1-methyl-1,2,4-triazol-3-yl;

$R^2$ is hydrogen, (1–6C)alkyl, (3–8C)cyclo-alkyl, (1–3C)alkyl(3–6C)cycloalkyl, (3–6C)cycloalkyl(1–3C)alkyl, (3–6C)alkenyl, optionally substituted by carboxy, (5–8C)cycloalkenyl, (3–6C)alkynyl, (2–5C)alkylcarbamoyl, phenylcarbamoyl, benzylcarbamoyl, (1–4C)alkylcarbamoyl(1–4C)alkyl, di(1–4C)alkyl carbamoyl(1–4C)alkyl, (1–4C)haloalkylcarbamoyl(1–4C) alkyl, triphenylmethyl, (1–3C)haloalkyl, (2–6C) hydroxyalkyl, (1–4C)alkoxy(2–4C)alkyl, (1–4C)alkylthio(2–4C)alkyl, (1–4C)alkanesulphinyl-(1–4C)alkyl, (1–4C)alkanesulphonyl(1–4C)alkyl, (2–6C)aminoalkyl, (1–4C)alkylamino(1–6C)alkyl, (2–8C)dialkylamino(2–6C) alkyl, (1–5C)cyanoalkyl, 3-amino-3-carboxypropyl, 2-(amidinothio)ethyl, 2-(N-aminoamidinothio)ethyl, tetrahydropyran-2-yl, thietan-3-yl, 2-oxopyrrolidinyl, or 2-oxotetrahydrofuran-3-yl, or $-R^2$ is the formula $-(CH_2)_n-R^6$ in which n is 1 to 4 and $R^6$ is piperidino, pyrrolidino, morpholino, piperazino or N-methylpiperazino, each value of $R^6$ being optionally substituted by (1–4C)alkyl, phenyl or benzyl, or $-R^2$ is of the formula $-(CH_2)_m-W-R^7$ in which m is 0 to 3, W is sulphur or a direct bond, and $R^7$ is phenyl or pyridinio(1–4C)alkylene or $R^7$ is pyridyl, imidazolyl, 1,3,4-thiadiazolyl, tetrazolyl, 1-(1–4C)alkyltetrazolyl, thiazolyl, isothiazolyl or isoxazolyl in which the link with W is via a carbon or uncharged nitrogen, each value of $R^7$ being optionally substituted, where possible, by one or two groups selected from (1–4C)alkyl, amino, hydroxy, carboxy, carbamoyl, nitro, (2–5C)alkoxycarbonyl, cyano or sulpho, or $R^2$ is of the formula $(CH_2)_n-CO-R^8$ in which n is 1 to 4 and $R^8$ is (1–4C)alkyl, phenyl or benzyl, or $-R^2$ is of the formula $-COR^9$ or $-(CH_2)_n-OCO-R^9$ in which n is 1–4 and $R^9$ is hydrogen, (1–4C)alkyl, (1–4C)haloalkyl, phenyl or benzyl, or $-R^2$ is of the formula $-G-CH_2-R^{10}$ in which G is carbonyl or a direct bond and $R^{10}$ is phthalimido, or $R^2$ is of the formula $-N^{\oplus}R^{11}R^{12}R^{13}$ in which $R^{11}$, $R^{12}$ and $R^{13}$ are (1–4C)alkyl, or $R^{11}$ is (1–4C)alkyl and $R^{12}$ and $R^{13}$ are joined to form a (3–6C)carbocyclic ring, or $R^{11}$, $R^{12}$ and $R^{13}$ are joined to form a 1-azonia-4- azabicyclo[2,2,2]octane or 1-azonia-3,5,7-triazatricyclo[3,3,1,13,7]decane, or R² is of the formula VI:

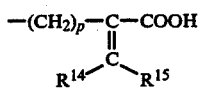

in which p is 1 or 2 and R¹⁴ and R¹⁵ are hydrogen or (1–6C)alkyl, or —R² is of the formula —P(O)R¹⁶R¹⁷ in which R¹⁶ is hydroxy, (1–4C)alkoxy, (2–8C)dialkylamino, phenoxy, phenylamino or one of the values given above for R⁶, and R¹⁷ is (1–4C)alkyl, (1–4C)alkoxy (2–8C) dialkylamino, phenoxy, phenylamino, piperidino, pyrrolidino, morpholino, piperazino or N-methylpiperazino, or —R² is of the formula —CH₂P(O)R¹⁸R¹⁹ in which R¹⁸ and R¹⁹ are hydroxy or (1–4C)alkoxy, or —R² is of the formula —CH(SR²⁰)COOR²¹ in which R²⁰ is (1–4C)alkyl and R²¹ is hydrogen or (1–6C)alkyl, or —R² is of the formula VII:

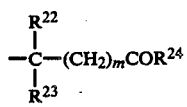

in which m is 0–3, R²² is hydrogen, (1–3C)alkyl or methylthio, R²³ is hydrogen, (1–3C)alkyl, (C₃–C₇)-cycloalkyl, cyano, carboxy, (2–5C)carboxyalkyl or methanesulphonylamino, or phenyl optionally substituted by amino or hydroxy, or R²² and R²³ are joined to form, together with the carbon to which they are attached, a (3–7C) carbocyclic ring, and R²⁴ is hydroxy, amino, (1–4C)alkoxy, (1–4C)alkylamino, phenylamino or of the formula R⁶ given above or of the formula NHOR²⁵ in which R²⁶ is hydrogen, (1–4C)alkyl, phenyl or benzyl, provided that when R² contains phenyl, and unless otherwise stated, the phenyl is optionally substituted by 1 or 2 groups selected from halogen, hydroxy, amino, carboxy, nitro, carbamoyl, cyano and aminomethyl.

A particular meaning for the group Q is a group of formula V wherein R¹ is 2-aminothiazol-4-yl or 5-amino-1,2,4-thiadiazol-3-yl and R² is (1–4C)alkyl, particularly where R² is methyl, or wherein R² is of the formula VII in which m is 0, R²⁴ is hydroxy and R²² and R²³ are (1–3C)alkyl groups, particularly where R²² and R²³ are both methyl, or R²² and R²³, together with the carbon atom to which they are attached, are joined to form a cyclobutyl or cyclopentyl group.

Where Q represents a precursor of a group required at the equivalent position in the final cephalosporin antibiotic it may for example represent such a group in which one or more functional groups are protected by suitable protecting groups, for example an amino group (e.g in a 2-aminothiazol-4-yl or 5-amino-1,2,4-thiadiazol-3-yl group) may be protected by an amino protecting group or a carboxyl group (for example when R² represents a group of formula VII in which R²⁴ is hydroxy) may be protected by a carboxyl protecting group. Such groups may be removed in subsequent conventional steps to yield the group Q required in the final cephalosporin antibiotic.

Alternatively Q may represent a group which requires one or more chemical reactions (other than conventional deprotection steps) to yield the group required. For example a precursor of the group of formula V may be a group of formula Va:

which may be converted into the group of formula V by reaction with a hydroxylamine derivative of formula H₂NOR₂.

Such a reaction is illustrated (where R² represents C(CH₃)₂ COOH or a protected form thereof) in published European Patent Application No. 160565.

Further examples of precursors of groups required at this position in cephalosporin antibiotics and processes for their transformation are given in Published European Patent Application Nos. 160563 and 160564.

Where Q represents an acylamino group not being a group required at the equivalent position in the final cephalosporin antibiotic or a precursor of such a group it preferably represents a substituted acetamido group, for example, a phenylacetamido group, a thien-2-ylacetamido group or a D-5-amino-5-carboxyvaleramido group. Such acetamido groups are to be found in the equivalent positions in the molecules of penicillin G, cephaloridine (a known cephalosporin antibiotic) and cephalosporin C respectively. Compounds containing such groups may be converted, by methods known in the art, to the corresponding 7-amino compounds. Such groups are accordingly equivalent in effect to amino protecting groups.

It will be readily understood that the group Q in the compounds of the formula II is protected, if necessary, to minimise the formation of by-products caused by reaction with the compound of the formula III. Such protection and subsequent deprotection is performed in conventional manner.

Compounds of formula I may be converted into the desired antibiotic cephalosporin derivatives (for example those described in European Patent Application No. 164944) by known methods, e.g. as descibed in the said European Patent Application No. 164944.

Thus, the heterocyclic substituent on the 3-aminomethyl group may be introduced by reacting the compound of formula I with the appropriate quaternary heterocycle, e.g. as shown in European Patent Application No. 164944.

Where the group Q is other than the group required in the final antibiotic compound the required group may be introduced or formed at any convenient stage of the reaction, either before or after the introduction of the heterocycle at the 3-position.

Where Q represents an amino protecting group or an acetamido group as discussed above this may be converted at any convenient stage to the compound of formula I wherein Q represents an amino group.

Introduction of the group Q required in the final antibiotic compound, or its precursor may be carried out by conventional techniques involving acylation of the compound of formula I wherein Q represents an amino group with an acylating agent, for example an acid of formula VIII:

(or a precursor therefor) or a reactive derivative thereof, e.g. the acid chloride or a thioester, in particular the benzothiazol-2-ylthioester as described in European Patent Application No. 37380.

The invention is illustrated, but not limited, by the following Examples. The NMR spectra are quoted in delta relative to tetramethylsilane (delta=0) as internal standard, (s=singlet, d=doublet, t=triplet, q=quartet, m=multiplet, br=broad). Temperatures are quoted in degrees Centigrade (Celsius).

7-ACA means 7-amino-3-acetoxymethylceph-3-em-4-carboxylic acid (7 aminocephalosporanic acid).

EAMACA means 7-amino-3-N-ethylaminomethyl-ceph-3-em-4-carboxylic acid. NBE means N-benzylidenethylamine and 1,3,5-THT means 1,3,5-triethyl-hexahydro-1,3,5-triazine. HPLC means high performance liquid chromatography; TLC means thin layer chromatography. DMF is dimethylformamide.

EXAMPLE 1

Method (A)

Hexamethyldisilane (1.35 g) was added dropwise to a stirred solution of iodine (2.34 g) in methylene chloride (3 ml) at room temperature in dried equipment under argon. The mixture was then refluxed for 16 h and cooled to 20° C. This solution was then added over 15 min to a suspension of 7-ACA (1 g) in methylene chloride (6 ml) containing NBE (2.44 g) at −5° C., keeping the temperature from rising above +5° C. On completion of the addition the mixture was allowed to warm up to 18° C. over 2 h. After cooling the reaction mixture back to −5° C. the second portion of NBE (1.5 g) was added in one portion, followed by epichlorohydrin (1.07 g). After stirring the mixture for 1.5 h at 0°–5° C. and then for 1.5 h at 5°–10° C. water (8 ml) was added. After 10 min vigorous stirring the upper aqueous phase was separated, and washed twice with methylene chloride (2×8 ml). p-Toluenesulphonic acid (0.47 g) was then added to the aqueous phase followed by isopropanol (40 ml) and the pH adjusted to 3 with concentrated hydrochloric acid. The mixture was then cooled to 0° C. and stirred for 15 min before adding a further portion of isopropanol (50 ml) over 1 h. The product was then filtered off, washed with acetone (2×10 ml) and dried in vacuo. to yield 646 mg EAMACA, p-toluene sulphonic acid salt. NMR (270 MHz; DMSO/TFA): 9.0 (1H,br.s); 8.54 (1H,br.s); 7.56 (2H,d J=8 Hz); 7.18 (2H, d J=8 Hz); 5.33 (1H d J=5 Hz); 5.27 (1H d J=5 Hz); 3.99 (2H,m); 3.82 (2H,s); 3.01 (2H,m); 2.33 (3H,s); 1.25 (3H,t), Method (B)

In dry equipment, under argon, hexamethyl-disilane (11.57 g) was added dropwise over 15 min to a stirred solution of iodine (20.08 g) in dichloromethane (30 ml) at reflux. The mixture was then refluxed for a further 2 h and stored overnight at 20° C. This solution was then added over 30 min to a suspension of 7-ACA (10 g) in dichloromethane (60 ml) containing NBE (24.5 g) at −5° C., keeping the temperature from rising above +5° C. On completion of the addition the mixture was allowed to warm up to 20° C. over 1.5 h. After cooling the reaction mixture back to −5° C., NBE (14.7 g) and then benzaldehyde (2.85 g) were added, and the mixture stirred for 30 min keeping the temperature below 5° C. Epichlorohydrin (10.7 g) was then added, maintaining the temperature below 5° C. After stirring for 3 h at 4° C. the mixture was allowed to warm up to 20° C. over 1 h then cooled back to 4° C. 2N HCl (25 ml) cooled to 4° C. was then added, maintaining the temperature below 10° C. After 10 min vigorous stirring at 5° C. the upper aqueous phase was separated, and washed twice with dichloromethane (2×80 ml). p-Toluenesulphonic acid (ca. 11 g) was then added to the aqueous phase until pH 1.8 at 10°–15° C., followed by isopropanol (125 ml) over 30 min. Triethylamine was then added until pH 3, followed by a second portion of isopropanol (125 ml) over 30 min at 0° C. After stirring for an additional hour at 0° C., the product was filtered off, washed with acetone (2×50 ml) and then dried in vacuo at room temperature. Yield 6.7 g EAMACA p-toluenesulphonic acid salt. NMR spectrum identical to that of the compound obtained by method (A).

In a manner similar to that of Example 1(B) a solution of trimethylsilyl iodide was prepared from hexamethydisilane (1.05 parts by weight) and iodine (1.82 parts by weight) in chloroform. This solution was added to a suspension of 7-ACA (1 part) in chloroform containing NBE (1.47 parts) keeping the temperature below −5° C. The mixture was allowed to warm, cooled to −5° C. and NBE (2.44 parts) and benzaldehyde (0.29 parts) were added. After 30 minutes epichlorohydrin (1.07 parts) was added. The reaction mixture was worked-up as in Example 1(B) to give EAMACA p-toluenesulphonic acid salt (0.87 parts by weight).

EXAMPLE 2

Method (A)

1,3,5-THT (0.106 ml, 0.55 mM) was added to a stirred solution of 7-amino-3-dimethylsulphoniomethyl-ceph-3-em-4-carboxylic acid di-trifluoromethylsulphonate (105 mg, 0.183 mM) in DMF (1 ml). After stirring for 15 min HPLC analysis showed the presence of EAMACA as the major product (by comparison with an authentic sample). Method (B)

7-Amino-3-dimethylsulphoniomethylceph-3-em-4-carboxylic acid di-trifluoromethylsulphonate (520 mg, 0.9 mM) was suspended in 1,2-dichloroethane (10 ml) stirring at room temperature. NBE (0.67 ml, 5.4 mM) was added rapidly and after a few minutes a clear yellow solution resulted. After 1 h HPLC analysis showed the presence of EAMACA as the major product (by comparison with an authentic sample).

EXAMPLE 3

Method (A)

To a stirred suspension of 7-ACA (3 mM) and NBE (15 mM) in $CH_2Cl_2$ (8 ml) at room temperature under argon was added trimethylsilyl trifluoromethanesulphonate (15 mM) over 10 min. The temperature was maintained at 25°–30° C. during the slight exotherm which resulted. After a further 2 h, HPLC analysis indicated that the reaction was complete. The mixture was cooled to 0° C., water (2 ml) added and the pH adjusted to 6.3 with $NaHCO_3$. p-Toluenesulphonic acid was added to bring the pH to 1.7 to 1.8, and isopropanol (10 ml) added. The solution was then adjusted to pH3 with triethylamine and a further aliquot of isopropanol (10 ml) added over 5 min. On stirring at 0° C., the product was obtained in 15% yield of EAMACA, p-toluene sulphonic acid salt. The NMR spectrum was identical to that of the product of Example 1.

Method(B)

Method(A) was repeated, substituting trimethylsilyl 1,1,2,2-tetrafluoroethanesulphonate for trimethylsilyl trifluoromethanesulphonate. The reaction time was 6 h and work-up with p-toluene-sulphonic acid as in Method (A) gave the EAMACA salt in a yield comparable with that of Method (A). The NMR spectrum was identical to that of the product of Example 1.

(C)7-ACA (1.84 mM) in dry $CH_2Cl_2$ (5 ml) was stirred with NBE (9.2 mM) as in Example 3(A) but using triisopropylsilyl trifluoromethanesulphonate (9.2 mM) instead of trimethylsilyl trifluoromethane sulphonate. The reaction mixture was stirred for 3 h, after which time water (2 ml) was added, followed by M tetra-n-butylammonium fluoride solution in tetrahydrofuran (2 ml). The aqueous phase was separated, washed with $CH_2Cl_2$ (2×10 ml) at less than 10° C. The pH was adjusted to 6.3 with triethylamine, followed by addition of p-toluene sulphonic acid to pH 1.7. Isopropanol (25 ml) was added dropwise to the rapidly stirred solution. The pH was adjusted to 3 with triethylamine and the solution cooled to 0° C. A further aliquot of isopropanol (25 ml) was added dropwise, the resulting precipitate filtered off, washed with acetone (2×5 ml) and dried at room temperature under vacuum to give EAMACA p-toluenesulphonic acid salt (239 mg, estimated purity 98%). NMR (200 MHz; $D_2O$/DCl); 1.4–1.55 (3H,t); 2.55 (3H,s); 3.2–3.4 (2H,q); 3.7–4.3 (4H,m) 5.35 (1H,d); 5.45 (1H,d), 7.5 (2H,d), 7.85 (2H,d).

Preparation of starting materials for Example 3

The trimethylsilyl and triisopropylsilyl reagents used in Example 3 were prepared as follows;

Trimethylsilyl trifluoromethanesulphonate

Method of M. Demuth and G Mikhail, *Synthesis*, 1982,827.

Trimethylsilyl 1,1,2,2-tetrafluoroethanesulphonate

Anhydrous 1,1,2,2-tetrafluoroethanesulphonic acid was prepared according to the method of Coffman et. al. (*J. Org. Chem.*, 1949, 14, 747) and converted to the trimethylsilyl derivative by the method of Demuth and Mikhail.

Triisopropylsilyl trifluoromethanesulphonate

Isopropyl magnesium chloride and trichlorosilane were reacted according to the method of *J. Org. Chem.*, 1980, 45,4797 to yield triisopropylsilane which was converted to the trifluoromethane sulphonate by the method of Demuth and Mikhail.

EXAMPLES 4–12

The imine reagents used in these Examples were prepared (unless otherwise indicated) by reacting the appropriate aldehyde or ketone (0.06M) in toluene (100 ml) with anhydrous ethylamine (0.09 M) under reflux in a Dean and Stark apparatus. The reactions were followed using infra-red spectroscopy, more ethylamine being added if necessary. 3 Angstrom molecular sieves were used to remove traces of water. The toluene was then distilled off and the residue distilled under reduced pressure. The boiling point of the imine was recorded.

Equivalent amounts of the imines thus produced were used instead of NBE in the process according to Example 3 (Method (A)) (results given in Table 1) or in the process according to Example 1 (Method (A)) (results given in Table 2). Any variations in procedure are indicated in the footnotes to the tables. The yield of EAMACA was estimated (for reactions in which EAMACA was not isolated) by comparing the peak area of EAMACA obtained by HPLC with the peak area obtained in Example 3 or Example 1.

TABLE 1

| Example No | Imine (R = NEt) R | B. Pt (°C./mmHg) | Relative Peak Area (EAMACA) by HPLC | Notes |
| --- | --- | --- | --- | --- |
| (3 Method (A)) | PhCH= | 65–67/9.0 | 1.0 | 1 |
| 4 | 2,4,6-trimethylphenyl-CH= | 74–81/0.6 | 1.2 | 2 |
| 5 | 4-$Bu^t$-phenyl-CH= | 85–88/4.5 | 0.4 | 3 |
| 6 | 2-$OSi(CH_3)_3$-phenyl-CH= | 72–76/1.0 | 0.8 | 4, 5 |

TABLE 1-continued

| Example No | Imine (R = NEt) R | B. Pt (°C./mmHg) | Relative Peak Area (EAMACA) by HPLC | Notes |
|---|---|---|---|---|
| 7 | 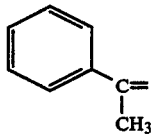 Ph-C(CH3)= | 75–80/2.0 | 0.1 | 6 |

Notes for Table 1
1 Results for Example 3 for comparison.
2 NMR (90 MHz CDCl₃): 1.2–1.4 (3H, t); 2.25 (3H, s); 2.3 (6H, s); 3.5–3.8 (2H, q); 6.8 (2H, s); 8.6 (1H, s).
3 NMR (90 MHz CDCl₃): 1.2–1.4 (12H, m); 3.5–3.8 (2H, q); 7.35–7.8(4H, q); 8.2(1H, s),
4 NMR (90 MHz CDCl₃): 1.3 (3H, t); 3.4 (2H, q); 6.75–7.4 (complex); 8.35 (1H, s).
5 The imine starting material was prepared as follows: - To a stirred solution of 2-hydroxybenzylimine (75 mM) in ether (30 ml) was added over 10 min N-trimethylsilylimidazole (82.5 mM). The reaction mixture was stirred at room temperature for 30 minutes, the precipitate filtered off, and the solvent removed. More imidazole was precipitated with cyclohexane. After filtration, the solution was evaporated and the residue distilled (yield 88%). NMR (90 MHzCDCl₃) 0.14 (9H, s); 1.15 (3H, t); 3.5 (2H, q); 6.6–7.3 (complex); 7.82 (1H, q); 8.55 (1H, s).
6 The imine starting material was prepared as described by F. Asinger, H. W. Becker, W. Schaefer and A. Saus, Monatsh. Chem., 1966, 97, 301. NMR (90 MHzCDCl₃): 1.3 (3H, t); 2.2 (3H, s); 3.42–3.65(2H, q); 7.25–7.4 (3H, m); 7.7–7.85 (2H, m).

TABLE 2

| Example No. | Imine R = NEt R | B. Pt °C./mmHg | Relative Peak Area (EAMACA) By HPLC | Notes |
|---|---|---|---|---|
| (1 method (A)) | PhCH= | 65–67/9 | 1.0 | 1 |
| 8 | 2,4,6-(CH₃)₃C₆H₂-CH= | 74–78/0.6 | 0.4 | |
| 9 | 4-Buᵗ-C₆H₄-CH= | 85–88/4.5 | 0.9 | |
| 10 | 4-NO₂-C₆H₄-CH= | — | 0.13 | 2 |
| 11 | 4-CH₃O-C₆H₄-CH= | 74/1.0 | 0.65 | 3 |
| 12 | Ph-C(CH₃)= | 75–80/2.0 | 0.3 | 4, 5, 6 |

NOTES FOR TABLE 2
1 Result for Example 1 for comparison.
2 Imine starting material has m.p. 76–7° C. (light petroleum). Prepared as described by F. B. Baddar, J. Chem. Soc., 1950, 136.
3 Imine starting material prepared as described by R. B. Moffett and W. M. Hoehn, J. Amer. Chem. Soc., 1947, 69, 1792
4 Yield of EAMACA (isolated as p-toluene sulphonic acid salt) was 8%.
5 Imine starting material prepared as described by B. L. Emling, J. E. Beatty, and J. R. Stevens, J. Amer. Chem. Soc., 1949, 71, 703.
6 Preparation as in Example 1, method (B).

EXAMPLES 13–18

EAMACA (p-toluenesulphonic acid salt) was prepared by the Seneral method of either Example 1 (Method (A)) or Example 3 (Method (A)) using, in place of 7-ACA, a 7-protected-amino cephalosporanic acid starting material prepared as described below. The yields of EAMACA obtained (expressed as HPLC peak area relative to the yield of either Example 1 or Example 3 respectively) are given in Tables 3 and 4.

7-(N-Benzylidenamino)cephalosporanic acid (Starting material for Examples 13 and 16)

A suspension of 7-ACA (6 mM), benzaldehyde (12 mM) and activated 4 Angstrom molecular sieve powder (2 g) was stirred in dry DMF (20 ml) at room temperature for 18 h under argon. The mixture was filtered and the solvent removed under vacuum. The product solidified on prolonged trituration with ether in 77% yield. NMR (200 MHz DMSO-$d_6$); 2.05 (3H,s); 3.55 (2H,q); 4.86(2H,q); 5.31 (1H,d); 5.65 (1H,q); 7.5–7.8 (5H, complex); 8.59(1H,d).

7-(N-[2-hydroxybenzyliden]amino)cephalosporanic acid (Starting material for Examples 14 and 17):

Prepared as for 7-(N-benzylideneamino)-cephalosporanic acid using 7-ACA and salicylaldehyde in 84% yield. NMR (200 MHzDMSO-$d_6$): 2.04(3H,s); 3.60(2H,q); 4.89(2H,q); 5.32(1H,d); 5.66(1H,d); 6.95–7.5(4H,complex); 7.95(1H,s); 8.78(1H,s).

7-(N-[4-nitrobenzyliden]amino)cephalosporanic acid (Starting material for Examples 15 and 18):

Prepared from 7-ACA (3 mM) and p-nitro-benzaldehyde (6 mM) in DMF (4 ml) by heating at 100° C. for 5 min under argon. On cooling, addition of ether (30 ml) caused the product to crystallise out as fluffy needles in 87% yield. Nmr (200 MHzDMSO-$d_6$): 2.04(3H,s); 3.58(2H,q); 4.87(2H,q); 5.35(1H,d); 5.76(1H,q); 8.03–8.32(4H,q); 8.75(1H,d).

TABLE 3

| Example No. | Relative Peak Area (EAMACA) by HPLC | Notes |
|---|---|---|
| 1 (comparison) | 1.0 | 1 |
| 13 | 0.2 | |
| 14 | 0.3 | |
| 15 | 0.2 | |

(General method of Example 1 (Method (A)) using starting materials as indicated above)

TABLE 4

| Example No. | Relative Peak Area (EAMACA) by HPLC | Notes |
|---|---|---|
| 3 (comparison) | 1.0 | 1 |
| 16 | 0.5 | |
| 17 | 0.75 | |
| 18 | 0.35 | |

(General method of Example 3 using starting materials as indicated above)

Notes for Tables 3 and 4
1. The method of Examples 1 and 3 was varied by allowing an additional equivalent each of NBE and trimethylsilyl iodide or trimethylsilyl trifluoromethane-sulphonate in order to silylate the phenolic hydroxyl group of the imine starting material.

EXAMPLE 19

To a slurry of 7-ACA (1.0 g) in methylene chloride at 0° C. under argon was added NBE (2.9 g) and then dropwise over 5 min trimethylsilyl iodide (3.68 g) which caused the temperature to rise to 14° C. The mixture was held at 0° C. for 3 h, warmed to 24° C. for ½ h and cooled to 0° C., when 1,3,5-THT (3.78 g) was added dropwise over 10 min. This addition caused the temperature to rise to 18° C.

Filtration of the resulting solution followed by analysis by HPLC indicated the presence of a 3-(1,3,5-triethylhexahydro-1,3,5-triziniummethyl)ceph-3-em intermediate in the reaction mixture by comparison with an authentic sample.

The filtrate was acidified to pH5 at 0° C. with 1N HCl, and pH2 with conc. HCl. The aqueous layer was separated, washed with methylene chloride (20 ml) and adjusted to pH5 with aqueous NaHCO$_3$ solution. After storage at −18° C. overnight EAMACA was identified in an estimated yield of 27% in solution by HPLC.

EXAMPLE 20

1,3,5-THT (0.420 ml, 2.2 mM) was added to a stirred suspension of 7-amino-3-iodomethyl-ceph-3-em-4-carboxylic acid (375 mg, 1.1 mM) in CH$_3$CN (3.5 ml). After 1 h more 1,3,5-THT (0.420 ml; 2.2 mM) was added and then ¾ h later water was added (0.600 ml; 33 mM). The mixture was filtered after stirring for ½ h, and the solvent evaporated from the filtrate under reduced pressure to give an oil. This was triturated with diethyl ether to produce a yellow solid which was filtered off in a dry bag to yield 568 mg of EAMACA. 506 mg had been obtained from an earlier preparation similar to the above.

The combined solids (1070 mg) were dissolved in 0.03M ammonium acetate (100 ml, pH adjusted to 6.0 with acetic acid) and pumped onto a column (450 mm×25 mm) of Diaion HP20 resin. The column was eluted with 0.03 m ammonium acetate solution. The fractions which were shown by HPLC to contain the product EAMACA were desalted by passing down a polystyrene resin column, eluting with water (200 ml) then with 10% v/v CH$_3$CN/H$_2$O. The fractions which were shown by HPLC to contain the product were evaporated under reduced pressure to low bulk and finally freeze dried to yield 164 mg of EAMACA as a pale yellow solid. NMR (200 MHzD$_2$O/DCl); 1.46 (t,3H) 3.32 (q,2H), 3.8, 4.0 (dd,2H) 3.93, 4.28 (dd,2H); 5.38 (d,1H); 5.48 (d,1H).

EXAMPLE 21

7-amino-3-(1,3,5-triethylhexahydro 1,3,5-triazinium)-methyl-ceph-3-em-4-carboxylic acid was prepared as follows: 7-amino-3-cyanothiomethyl ceph-3-em-4-carboxylic acid (12 g) was suspended in DMF (120 ml) and the stirred suspension treated, at room temperature, with 1,3,5-THT (15.1 g, 16.94 ml) and diisopropylethylamine (11.4 g, 15.40 ml). After 10 min a clear solution was obtained. After a further 20 min the DMF was evaporated under reduced pressure and the residue triturated with CH$_3$CN and Et$_2$O. The solid so obtained was filtered off, washed with Et$_2$O and dried. Yield 13.33 g (78%). The above compound (700 mg) was dissolved in the minimum volume of a mixture of glacial acetic and water (1:1) and acetonitrile added until precipitation of the solid was complete. The solid was filtered off, washed with CH$_3$CN and Et$_2$O and dried to yield 440 mg (94%) EAMACA. NMR (200 MHz.DCl+D$_2$O); 1.42 (t,3H); 3.30 (d,1H) 3.38 (d,1H); 3.81 (d,1H) 3.96 (d,1H); 4.05 (d,1H) 4.3(d,1H); 5.39 (d,1H); 5.47 (d,1H).

EXAMPLE 22

A stirred suspension of 7-amino-3-cyanothiomethyl-ceph-3-em-4-carboxylic acid (1 g) in DMF (10 ml) was treated with 1,3,5-THT (0.7 g, 0.785 ml) and quickly thereafter with diisopropylethylamine (1.7 g, 1.9 ml). A clear solution was obtained within ten minutes. After stirring for 1 h the mixture was concentrated under reduced pressure and the residue triturated with CH$_3$CN. The solid obtained was washed with CH$_3$CN and with ether and dried (0.88 g). The solid was dissolved in 5% H$_2$O in CH$_3$CN (20 ml) containing glacial acetic acid (4 ml) and the solution applied to a silica column (25 mm×300 mm). The column was subjected to graded elution (5–50% H$_2$O) and the appropriate fractions evaporated to give 380 mg, (40%) of EAMACA. NMR (200 MHzDCl+D$_2$O): 1.48(t,3H); 3.30(d,1H); 3.38 (d,1H); 3.82 (d,1H); 3.95 (d,1H); 4.05 (d,1H); 4.29 (d,1H); 5.39 (d,1H); 5.48 (d,1H).

EXAMPLE 23

(a) 7-[2-(2-tritylaminothiazol-4-yl)-2((Z)-1-t-butoxycarbonyl-1-methylethoxyimino)acetamido]-3-cyanothiomethylceph-3-em-4-carboxylic acid (10 g) was dissolved in CH$_3$CN (100 ml) and treated, quickly, dropwise at room temperature, with a mixture of 1,3,5-THT (4.2 g, 4.6 ml) and diisopropylamine (3.1 g, 4.1 ml). After 15 min at room temperature the solution was poured into a mixture of toluene (500 ml) and glacial acetic acid (50 ml) and extracted several times with brine. The organic phase was dried over MgSO$_4$, filtered through celite and evaporated to give a foam. Trituration of the foam with ether gave 3-ethylaminomethyl-7-[2-(2-tritylamino-thiazol-4-yl)-2((Z)-1-t-butoxycarbonyl-1-methylethoxy-imino)-acetamido]ceph-3-em-4-carboxylic acid as a granular solid (9.08 g, 92% yield) NMR (200 MHzd$_6$DMSO+CD$_3$COOD): 1.17(t,3H); 1.32(s,9H); 1.39(s,3H); 1.40(s,3H); 2.96(q,2H); 3.54(d,1H); 3.59(d,1H); 3.65(d,1H); 3.86(d,1H); 5.08(d,1H); 5.69(d,1H); 6.68(s,1H); 7.1–7.4(m,15H).

(b) The product of (a) above (9.0 g) was dissolved in formic acid (40 ml) and conc. HCl (3 ml) was added dropwise to the solution. After 3 h at room temperature the mixture was poured into butan-2-one (150 ml) and t-butylmethyl ether (50 ml) was then added to precipitate the product which was filtered off, washed with butan-2-one and t butylmethyl ether, and dried to yield 3-ethylaminomethyl-7-[(2-aminothiazol-4-yl)-2-((Z)-1-carboxy-1-methylethoxyimino)acetamido]ceph-3-em-4-carboxylic acid (5.73 g, 99% yield). NMR(200 MHzd$_6$DMSO+CD$_3$COOD): 1.2(t,3H); 1.49(s,3H) 1.51(s,3H); 2.94(d,1H) 2.97(d,1H); 3.69(d,1H); 3.71(d,1H); 3.77(d,1H); 3.86(d,1H); 3.91(d,1H); 5.15(d,1H); 5.89(d,1H); 6.94(s,1H).

EXAMPLE 24

(a) To a stirred suspension of 7-amino-3-cyanothiomethylceph-3-em-4-carboxylic acid (18.6 g) in anhydrous CH$_2$Cl$_2$ (250 ml) was added bis(trimethylsilyl)acetamide (27 ml) under an atmosphere of argon. The mixture was stirred for 1 h to give a yellow solution, which was added over 15 min to a stirred solution of 2-((Z)-1-t-butoxycarbonyl-1-methylethoxyimino)-2-(2-tritylaminothiazol-4-yl)acetyl chloride hydrochloride (31.2 g) and 2,6-lutidine (11.6 ml) in anhydrous methylene chloride (500 ml) at 0° C. under an atmosphere of argon. The reaction mixture was allowed to warm to room temperature and stirred for 90 min, then cooled back to 0° C. Methanol (50 ml) was added and stirring was continued for a further 30 min. The resulting cloudy solution was washed with water (2×250 ml) and dried (Na$_2$SO$_4$). The solvent was evaporated under reduced pressure to yield a buff foam. This was triturated with ether to yield a pale buff amorphous solid, 7-(2-((Z)-1-t-butoxycarbonyl-1-methylethoxyimino)-2-(2-tritylaminothiazol-4-yl)acetamido)-3-cyanothiomethylceph-em-4-carboxylic acid which was filtered off and dried under vacuum to give a yield of 39.8 g. NMR (200 MHzd$_6$DMSO-CD$_3$CO$_2$D): 1.30(s,9H); 1.40 (s,6H); 3.46(d,1H); 3.73(d,1H); 4.12(d,1H); 4.21(d,1H); 5.14(d,1H); 5.73(d,1H); 6.67(s,1H); 7.25(m,15H).

(b) The product of (a) above (10.26 g) was powdered and added to formic acid (41 ml) at 0° C. with stirring. Concentrated hydrochloric acid (3.06 ml) was added over 5 min and the mixture was stirred for 75 min whilst allowing it to warm to room temperature. The reaction mixture was recooled to 0° C. and filtered through a glass sinter to remove the white precipitate. The filtrate was evaporated under reduced pressure to give an orange gum which was triturated with ethyl acetate to yield an off-white amorphous solid, the hydrochloride salt of 7-(2-(2-aminothiazol-4-yl)-2-((Z)-1-carboxy-1-methylethoxyimino)-acetamido-3-cyanothiomethylceph-3-em-4-carboxylic acid which was filtered off and dried under vacuum to give a yield of 6.77 g. NMR (200 MHZd$_6$DMSO-CD$_3$CO$_2$D): 1.50(d,6H); 3.53(d,1H); 3.78(d,1H); 4.17(s,2H), 5 21(d,1H) 5.84(d,1H); 6.96(s,1H).

(c) A solution of the product of (b) above (562 mg) in DMF (4 ml) was stirred at −10° C. To this solution was added 1,3,5-THT (0.192 ml) followed by diisopropylethylamine (0.523 ml) and the solution stirred for a further 15 min. The DMF was evaporated under reduced pressure and the gummy residue . triturated with acetonitrile (10 ml) to give a pale yellow amorphous solid, the bis-diisopropylethylamine salt of 7-(2-(2-aminothiazol-4-yl)-2-((Z)-1-carboxy-1-methylethoxyimino)-acetamido-3-ethylaminomethylceph-3-em-4-carboxylic acid, which was filtered off and dried under vacuum to give a yield of 340 mg, of estimated purity 47%. NMR (200MHZd$_6$DMSO-CD$_3$CO$_2$D): 0.95–1.30 (m,33H); 1.45(d,6H); 2.60–3.00(m,11H); 3.40–4.00(m,4H); 5.05(d,1H); 5.80(d,1H) 6.73(s,1H).

EXAMPLE 25

15 Ethylamine adsorbed on activated charcoal (270 mg; 0.2 mM EtNH$_2$) was added to a solution of 3-cyanothiomethyl-7-[2-(2-tritylaminothiazol-4-yl)-2-((Z)-1-t-butoxycarbonyl-1-methylethoxyimino)acetamido]ceph-3-em-4-carboxylic acid. (73 mg; 0.09 mM) in acetonitrile (2 ml). HPLC analysis showed the presence of 3-ethylaminomethyl-7-[2-(2-tritylaminothiazol-4-yl)-2-((Z)-1-t-butoxycarbonyl-1-methylethoxyimino) acetamido]ceph-3-em-4-carboxylic acid (by comparison with an authentic sample).

EXAMPLE 26

2-((Z)-1-t-butoxycarbonyl-1-methylethoxyimino-2-(2-tritylaminothiazol-4-yl)acetamido-3-hydroxymethyl-ceph-3-em-4-carboxylic acid (1.96 g) was dissolved in a mixture of acetonitrile (10 ml) and formamide (2.5 ml). The solution was cooled under argon to −30° C. to form a thick gel. NBE (1 g) was added followed by a dropwise addition of methyl o-phenylenephosphate (0.93 g) in methylene chloride (2.5 ml) over 6 mins at −30° C. to −35° C. After complete addition the resulting pale brown suspension was stirred at −35° C. for 10 min and then slowly warmed to 20°–25° C. for 20 min. During this time the solid dissolved and the resulting solution darkened (at about −10° C.) On further warming the solution became paler until it was orange/yellow. TLC analysis confirmed the formation of the required product, 2-((Z)-1-t-butoxycarbonyl-1-methylethoxyimino)-2-(2-tritylaminothiazol-4-yl)acetamido-3-N-ethylamino-methylceph-3-em-4-carboxylic acid. Water (2.5 ml) was added and the solvent was evaporated under reduced pressure to leave a gum. The gum was partitioned between $CH_2Cl_2$ (25 ml) and water 25 ml). The $CH_2Cl_2$ layer was separated and dried over $MgSO_4$ and then evaporated under reduced pressure to a gum. The gum was triturated with ether and the resulting solid, collected by filtration, washed with further ether and dried under reduced pressure to yield 2.09 g of a beige coloured powder. This was purified by chromatography on silica. The product rich fractions were combined and evaporated under reduced pressure to leave a gum. This was azeotroped under reduced pressure with tetrachloro-ethylene and the remaining gum was triturated with ether to yield 0.1491 g of an off white, partially crystalline powder. A small sample of the purified product was de-protected using trifluoro-acetic acid. After drowning into water and removing triphenylmethanol by HPLC the product was shown to have an identical HPLC retention time to the product of Example 23(b).

EXAMPLE 27

7-ACA (6 g) was suspended in dry dichloromethane (54 ml) at 0° C. under a nitrogen atmosphere. NBE (18.6 ml) was added quickly, followed by trimethylsilyliodide (15.6 ml) over 10 min. After 2 h at 0° C. and 15 min at ambient temperature a second portion of NBE (18.6 ml) was added and the mixture left for 1 h at 0° C. Water (1.2 ml) was added and the temperature maintained at 0° C. After 2 h, 1N HCl (150 ml) was added and the mixture stirred vigorously for 30 min. The aqueous phase was decanted and washed with two portions of dichloromethane. The pH was adjusted to 5 with solid sodium bicarbonate and the solution was purified by chromatography on HP 20 SS polystyrene resin, the product eluting in water. The pure fractions were concentrated and the residue dissolved in a little methanol. The product (EAMACA) was precipitated from ether as a white powder (1.8 g). The NMR spectrum was substantially identical to that obtained for the product of Example 1.

EXAMPLE 28

(a) 4'-Methoxybenzyl 7-amino-3-chloromethylceph-3-em-4-carboxylate toluene-4 sulphonate acid salt (5.0 g) was added to formic acid (20 ml) and the solution heated to 45° C. for 2 hours, with good agitation, under an atmosphere of argon. The solution was cooled to room temperature and poured into acetone (200 ml). Solid began to crystallise after a few minutes, the mixture was cooled in an ice bath for 20 minutes, filtered and the solid was washed with acetone and dried under vacuum to give 7-amino-3-chloromethyl-ceph-3-em-4-carboxylic acid toluene-4-sulphonic acid salt (2.83 g).

(b) The product of (a) (0.1 g) was suspended in acetonitrile (2.0 ml). Benzaldehyde (90 μl) and subsequently bis(trimethylsilyl)acetamide (199 μl) were added, under an argon atmosphere, and the mixture was stirred at room temperature for 90 minutes. NBE (287 μl) was added and the reaction mixture was stirred overnight at room temperature. 1N Hydrochloric acid (5 ml) and dichloromethane (5 ml) were added, the reaction mixture was stirred for 5 minutes, allowed to settle and the aqueous layer separated. HPLC analysis of the aqueous layer showed the presence of EAMACA with a retention time identical to that of an authentic sample. The estimated yield of EAMACA in solution was 17%.

EXAMPLE 29

(a) 7-Amino-3-chloromethyl-ceph-3-em-4-carboxylic acid toluene-4-sulphonic acid salt (1.0 g) was suspended in acetonitrile (5 ml) and cooled to 10°–15° C. 1,3,5-Hexahydro-1,3,5-triethyltriazine (0.45 ml) and subsequently diisopropylethylamine (1.28 ml) were added dropwise. The mixture was allowed to warm to room temperature, stirred for 2 hours, poured into acetone (50 ml) and a solid precipitated. The mixture was stirred in an ice-bath for 15 minutes; the solid was filtered, washed with acetone and dried under vacuum to give 7-amino-3(1,3,5-hexahydro-1,3,5-triethyltriazinium)-methyl-ceph-3-em-4-carboxylic acid (0.68 g).

(b) The product of a) above (0.68 g) and toluene-4-sulphonic acid (0.44 g) were suspended in isopropanol (2.7 ml) and water (0.7 ml). The mixture was warmed to give a solution, which was cooled, seeded and stored at 5° C. The resultant crystals were collected, washed with aqueous isopropanol ($H_2O$; PrOH; 100:25 v/v) and dried under vacuum to give EAMACA toluene-4-sulphonic acid salt (0.084 g), identical with an authentic sample.

We claim:
1. A process for the preparation of the compounds of the formula (I):

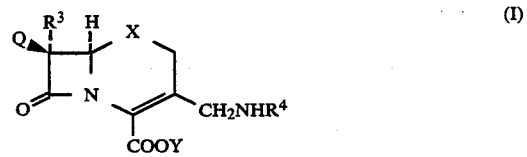

or a salt thereof wherein
X is sulphur, oxygen, methylene or sulphinyl (R or S configuration);
$R^3$ is hydrogen or methoxy;
$R^4$ is (1–4C)alkyl, halo(1–4C)alkyl, hydroxy(1–4C)alkyl, (1–4C)alkoxy(1–4C)alkyl, carboxy(1–4C)alkyl, amino (1–4C)alkyl, cyano(1–4C)alkyl, (1–4C)alkanoyl-amino(1–4C)alkyl, allyl, furfuryl, benzyl or pyridyl-(1–4C)alkyl;
Y is hydrogen or a carboxyl protecting group; and
Q has one of the following meanings;
  (i) an amino group;
  (ii) a protected amino group;
  (iii) a group required at the equivalent position in the final cephalosporin antibiotic or a precursor of such a group;
  (iv) an acylamino group not falling within (iii) above but which can readily be converted to an amino group;
which process comprises reacting a compound of formula (II):

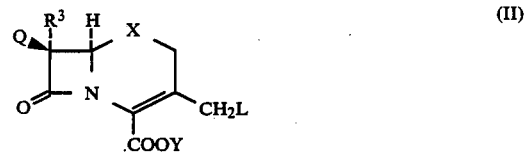

wherein Q, X, Y and $R^3$ are as hereinbefore defined and L is an acyloxy, halogen, carbamoyloxy, alkylthio, cyanothio, dialkylsulphonio, substituted-alkane, sulphonyloxy or o-phenylenephosphonyloxy group, with a compound of the formula (III):

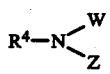   (III)

wherein $R^4$ is as hereinbefore defined and W and Z independently represent hydrogen atoms or W and Z independently represent a group $ArCH_2$, $Ar_2CH$, ArS, a sulphonyloxy group, a carboxy group or a silyl moiety wherein Ar represents a phenyl, thienyl or furyl group any of which is optionally substituted by one or more groups selected from halogen, nitro, cyano, (1–6C)alkyl, hydroxy, amino, (1–4C)alkoxy, carboxy, (2–6C)alkoxycarbonyl, carbamoyl, mono- or di(1–4C)alkylcarbamoyl and aminomethyl, or one of W and Z represents such a group and the other is hydrogen; or W and Z are joined to form a triazine of the formula IV:

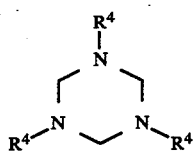   (IV)

wherein $R^4$ is as defined hereinabove or a compound of formula IVa

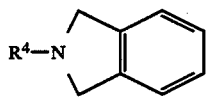   (IVa)

wherein $R^4$ is as defined hereinabove or IVb:

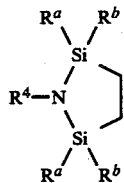   (IVb)

wherein $R^4$ is as defined hereinabove, and $R^a$ and $R^b$ are $C_{1-4}$ alkyl groups; or W and Z together represent an alkylidene group or a group of the formula $ArCH=$, $ArC(R^a)=$ or $(Ar)_3P=$ wherein Ar and $R^a$ are as hereinbefore defined or a group of formula IVc

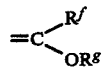   (IVc)

wherein $R^f$ and $R^g$ represent (1–4C)alkyl groups, to yield a compound of the formula (I).

2. A process according to claim 1 wherein W and Z (which may be the same or different) represent a group $ArCH_2$, $Ar_2CH$, ArS, a sulphonyloxy group, a carboxy group or a silyl moiety wherein Ar represents a phenyl, thienyl or furyl group any of which is optionally substituted by one or more groups selected from halogen, nitro, cyano (1–6C)alkyl, hydroxy, amino, (1–4C)alkoxy, carboxy, (2–6C)alkoxycarbonyl, carbamoyl, mono or di(1–4C)alkylcarbamoyl and aminomethyl; or one of W and Z represents such a group and the other is hydrogen; or W and Z are joined to form a triazine of the formula IV:

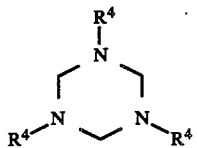   (IV)

wherein $R^4$ is as defined in claim 1 or a compound of formula IVa

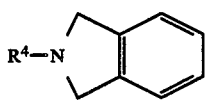   (IVa)

wherein $R^4$ is as defined in claim 1 or IVb

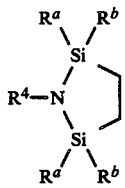   (IVb)

wherein $R^4$ is as defined in claim 1 and $R^a$ and $R^b$ are $C_{1-4}$ alkyl groups; or W and Z together an alkylidene group or a group of the formula $ArCH=$, $ArC(R^a)=$ or $(Ar)_3P=$ wherein Ar and $R^a$ are as hereinbefore defined or a group of formula IVc

   (IVc)

wherein $R^f$ and $R^g$ represent (1–4C)alkyl groups.

3. A process according to claim 1 wherein W represent hydrogen and Z represents a group $ArCH_2$ wherein Ar represents phenyl or phenyl substituted by one or more groups selected from halogen, nitro, cyano, (1–6C)alkyl, hydroxy, amino, (1–4C)alkoxy, carboxy, (2–6C)alkoxycarbonyl, carbamoyl, mono- or di(1–4C)alkylcarbamoyl and aminomethyl.

4. A process according to claim 1 wherein W and Z are joined to form a triazine of formula IV, as defined in claim 2.

5. A process according to claim 1 wherein W and Z together represent a group $ArCH=$ wherein Ar represents phenyl or phenyl substituted by one or more groups selected from halogen, nitro, cyano (1–6C)alkyl, hydroxy, amino, (1–4C)alkoxy, carboxy, (2–6C)alkoxycarbonyl, carbamoyl, mono- or di(1–4C)alkylcarbamoyl and aminomethyl.

6. A process according to claim 1 wherein the leaving group L is an acetoxy group, and the reaction is carried out in the presence of iodide or thiocyanate ions.

7. A process according to claim 1 wherein L is an acetoxy group and the reaction is carried out in the presence of a trialkylsilyl iodide.

8. A process according to claim 1 wherein L is an acetoxy group, and the reaction is carried out in the presence of an alkane sulphonate derivative.

9. A process according to claim 1 carried out in the presence of an epichlorohydrin.

* * * * *